(12) United States Patent
Gandara et al.

(10) Patent No.: US 9,970,912 B2
(45) Date of Patent: May 15, 2018

(54) MODULAR SMOKE DETECTION SYSTEM

(71) Applicant: UTC FIRE & SECURITY AMERICAS CORPORATION, INC., Bradenton, FL (US)

(72) Inventors: Miguel Angel Perez Gandara, Barcelona (ES); David Gimenez, Barcelona (ES)

(73) Assignee: UTC FIRE & SECURITY AMERICAS CORPORATION, INC., Bradenton, FL (US)

( * ) Notice: Subject to any disclaimer, the term of this patent is extended or adjusted under 35 U.S.C. 154(b) by 537 days.

(21) Appl. No.: 14/431,337

(22) PCT Filed: Sep. 24, 2013

(86) PCT No.: PCT/US2013/061497
§ 371 (c)(1),
(2) Date: Mar. 26, 2015

(87) PCT Pub. No.: WO2014/052340
PCT Pub. Date: Apr. 3, 2014

(65) Prior Publication Data
US 2015/0241398 A1  Aug. 27, 2015

(30) Foreign Application Priority Data
Sep. 27, 2012  (ES) .................................. 201231497

(51) Int. Cl.
*G01N 33/00* (2006.01)
*G01N 1/26* (2006.01)
(Continued)

(52) U.S. Cl.
CPC ........... *G01N 33/0036* (2013.01); *G01N 1/26* (2013.01); *G08B 17/10* (2013.01); *G08B 17/113* (2013.01); *G08B 25/14* (2013.01)

(58) Field of Classification Search
CPC ...... G01N 33/0036; G01N 1/26; G08B 17/10; G08B 17/113; G08B 25/14
(Continued)

(56) References Cited

U.S. PATENT DOCUMENTS 3,676,570 A  7/1972  Gabb
4,238,679 A  12/1980  MacMillan et al.
(Continued)

FOREIGN PATENT DOCUMENTS

DE   102010003952 A1   10/2011
EP       0233294 A1    8/1987
(Continued)

OTHER PUBLICATIONS

Watlow Electric, Inc. "EZ Zone RM Limit Module User's Guide", Sep. 2010, 100 pages.
(Continued)

*Primary Examiner* — Daniel S Larkin
(74) *Attorney, Agent, or Firm* — Cantor Colburn LLP

(57) ABSTRACT

Apparatus and methods for detecting smoke in an area. The apparatus may include a first detector module comprising a sensor configured to detect smoke in a volume of air received from the area, and a display module configured to receive input from the first detector module and provide output to a detection management device. The apparatus may also include a first backplane electrically coupled to the first detector module, and a second backplane electrically coupled to the display module and to the first backplane so as to transmit power, signals, or both between the display module and the first detector module. The first and second backplanes may be interchangeable.

20 Claims, 5 Drawing Sheets

(51) Int. Cl.
*G08B 17/10* (2006.01)
*G08B 25/14* (2006.01)
*G08B 17/113* (2006.01)

(58) Field of Classification Search
USPC ............ 73/31.01, 31.02, 31.03, 31.05
See application file for complete search history.

(56) References Cited

U.S. PATENT DOCUMENTS

| | | |
|---|---|---|
| 4,286,159 A | 8/1981 | Kitta et al. |
| 4,785,288 A | 11/1988 | Heberlein, Jr. et al. |
| 4,887,073 A | 12/1989 | Nakao et al. |
| 5,403,198 A | 4/1995 | Koganemaru |
| 5,478,256 A | 12/1995 | Koganemaru et al. |
| 5,563,766 A | 10/1996 | Long et al. |
| 5,577,696 A | 11/1996 | Kramer |
| 5,612,678 A | 3/1997 | Shibata |
| 6,057,774 A | 5/2000 | Venzant |
| 6,057,778 A | 5/2000 | Davidson |
| 6,273,388 B1 | 8/2001 | Capaldi-Tallon |
| 6,288,647 B1 | 9/2001 | Yamano |
| 6,300,876 B1 | 10/2001 | Sakurai et al. |
| 6,377,182 B1 | 4/2002 | Devine et al. |
| 6,737,977 B2 | 5/2004 | Nishikawa et al. |
| 6,778,091 B2 | 8/2004 | Qualey, III et al. |
| 6,819,257 B2 | 11/2004 | Swieboda et al. |
| 6,953,936 B2 | 10/2005 | MacPherson, III et al. |
| 7,026,948 B1 | 4/2006 | Rutter et al. |
| 7,287,738 B2 | 10/2007 | Pitlor |
| 7,414,538 B2 | 8/2008 | Cook et al. |
| 7,463,159 B2 | 12/2008 | Hess et al. |
| 7,525,445 B2 | 4/2009 | Deluca et al. |
| 7,696,896 B2 | 4/2010 | Siber et al. |
| 7,786,888 B2 | 8/2010 | Luterotti et al. |
| 7,969,321 B2 | 6/2011 | Spellman |
| 8,089,769 B2 | 1/2012 | Casey |
| 8,106,784 B2 | 1/2012 | Katou |
| 2003/0212508 A1 | 11/2003 | Bibelhausen et al. |
| 2004/0155786 A1 | 8/2004 | Guttinger et al. |
| 2006/0109136 A1 | 5/2006 | Sumlin et al. |
| 2007/0103325 A1 | 5/2007 | Wagner et al. |
| 2012/0050030 A1 | 3/2012 | Murphy et al. |

FOREIGN PATENT DOCUMENTS

| | | |
|---|---|---|
| EP | 0707207 A2 | 4/1996 |
| EP | 1039427 A1 | 9/2000 |
| EP | 1258848 A2 | 11/2002 |
| EP | 1413997 A2 | 4/2004 |
| EP | 2402920 A2 | 1/2012 |
| FR | 2607938 A1 | 6/1988 |
| GB | 2278719 A | 12/1994 |
| GB | 1306218 A | 4/1997 |
| JP | H03183196 A | 8/1991 |
| JP | 2002109650 A | 4/2002 |
| JP | 2007052708 A | 3/2007 |
| JP | 2007257107 A | 10/2007 |
| JP | 2009245088 A | 10/2009 |
| JP | 2009245123 A | 10/2009 |
| WO | 9621208 A1 | 7/1996 |
| WO | 9705586 A1 | 2/1997 |
| WO | 9705587 A1 | 2/1997 |
| WO | 0143098 A2 | 6/2001 |
| WO | 2009082246 A1 | 7/2009 |
| WO | 2009115720 A2 | 9/2009 |
| WO | 2010083839 A1 | 7/2010 |

OTHER PUBLICATIONS

International Search Report and Written Opinion for application PCT/US2013/061497, dated Feb. 4, 2014, 8 pages.

Spanish search report for application ES 201231497, dated May 26, 2014, 7 pages.

MODULAR SMOKE DETECTION SYSTEM

CROSS-REFERENCE TO RELATED APPLICATION

This application claims priority to Spanish Patent Application No. 201231497, filed on Sep. 27, 2012. The entirety of this priority patent application is incorporated herein by reference.

BACKGROUND

High Sensitivity Smoke Detector (HSSD) systems are typically positioned proximal a protected area in a building and configured to monitor the protected area for smoke. These systems generally include an aspirating fan to draw air from a protected area via a network of sampling pipes and sampling holes. The sampled air is then passed through a high-sensitivity, precision detector that analyzes the air and generates a warning signal when appropriate (e.g., when smoke or combustion gasses are present). Two or more of such systems may be linked together to share information, but each system is generally self-contained, requiring its own power source. The systems communicate with one another, and with other devices, over a network and may be monitored by a user and/or an automated system.

Installation of such precision systems presents several challenges. For example, dust created by construction activities may have a negative impact on the life cycle of the precision equipment of the HSSD systems. However, it is often inconvenient to install a system after construction is complete, given the positioning of electrical conduits, etc., typically required for complete installation. Furthermore, such HSSD systems are typically not scalable. Each detector is generally configured to receive a single air stream and provide information related thereto to a master controller over the network. Accordingly, each protected area requires its own detector and input/output controller.

What is needed are improved apparatus and methods for detecting smoke in a protected area.

SUMMARY

Embodiments of the disclosure may provide an apparatus for detecting smoke in a protected area. The apparatus includes a first detector module including a sensor configured to detect smoke in a first volume of air received from the protected area. The apparatus includes a second detector module including a sensor configured to detect smoke in a second volume of air received from the protected area. The apparatus includes a first backplane electrically coupled to the first detector module. The apparatus also includes a second backplane electrically coupled to the second detector module and to the first backplane so as to transmit power, signals, or both between the first and second detector modules, wherein the first and second backplanes are interchangeable and the first and second detector modules are interchangeable.

Embodiments of the disclosure may also provide a method for detecting smoke in a protected area. The method may include selecting a number of detector modules, with the number of detector modules corresponding to a selected number of channels for the smoke detector. The detector modules may each being configured to receive air from a protected area and to detect smoke therein. The method may also include selecting a number of backplanes, with the number of backplanes being at least one more than the number of detector modules. Further, the backplanes may be interchangeable. The method may also include connecting the backplanes together such that the backplanes are at least electrically coupled together, and coupling the detector modules to the backplanes, wherein each detector module is coupled to a separate one of the backplanes. The method may further include coupling the display module to one of the backplanes, wherein the display module is communicable with the detector modules via two or more of the backplanes.

BRIEF DESCRIPTION OF THE DRAWINGS

The accompanying drawings, which are incorporated in and constitute a part of this specification, illustrate aspects of the present teachings and together with the description, serve to explain principles of the present teachings. In the figures.

DETAILED DESCRIPTION

Reference will now be made in detail to various embodiments of the present teachings, an example of which is illustrated in the accompanying drawings. Wherever possible, the same reference numbers will be used throughout the drawings to refer to the same or like parts.

In the following description, reference is made to the accompanying drawings that form a part thereof, and in which is shown by way of illustration specific implementations in which may be practiced. These implementations are described in sufficient detail to enable those skilled in the art to practice these implementations and it is to be understood that other implementations may be utilized and that changes may be made without departing from the scope of the present teachings. The following description is, therefore, merely exemplary.

Figure 1:
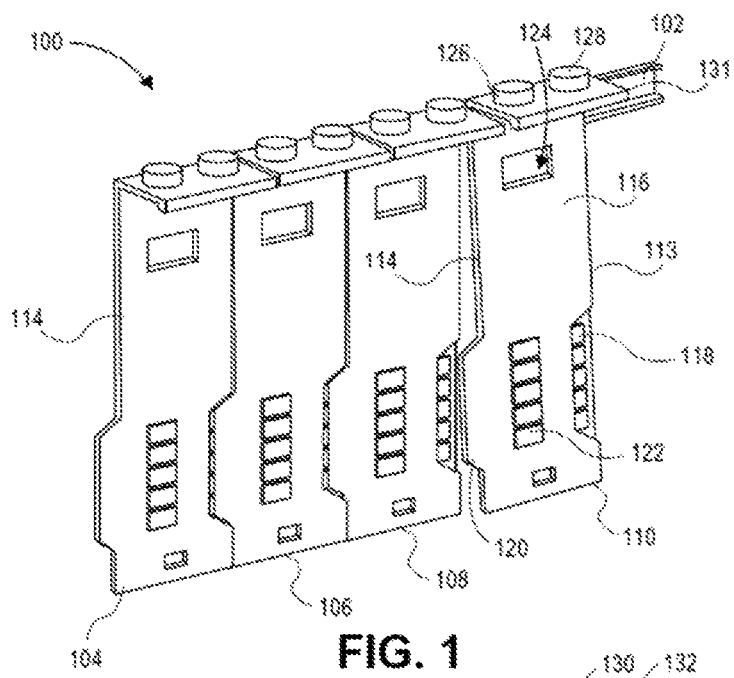
FIG. 1 illustrates a perspective view of a partially-assembled smoke detection system, depicting backplanes thereof being assembled with a rail, according to an embodiment.
Figure 2:
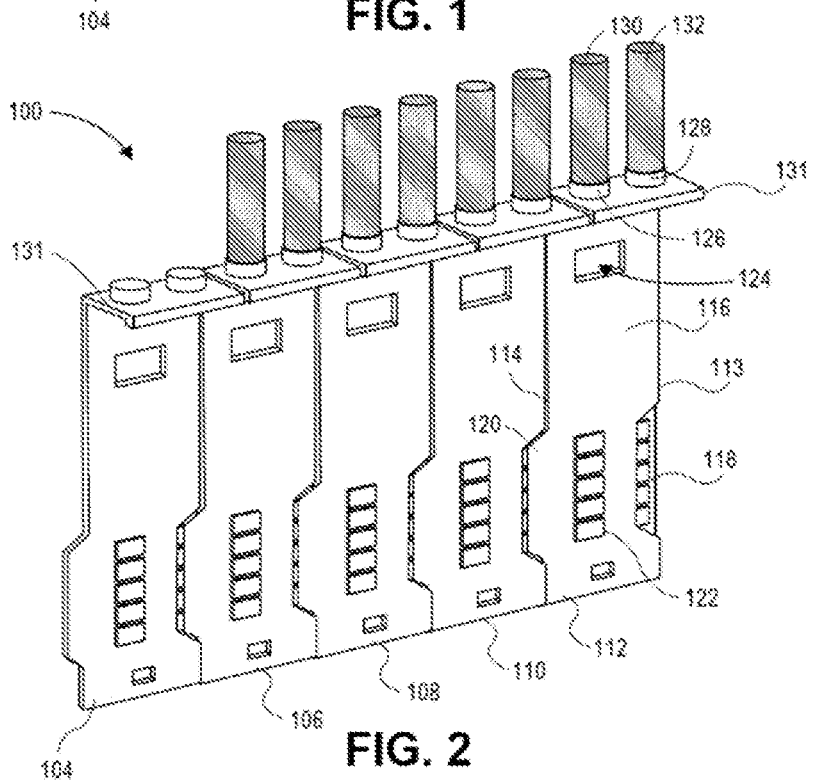
FIG. 2 illustrates another perspective view of the partially-assembled smoke detection system, depicting an additional backplane and inlet and outlet conduits coupled with the backplanes, according to an embodiment.

FIGS. 1 and 2 illustrate perspective views of a partially-assembled smoke detection system 100 (hereinafter, "system 100"), according to an embodiment. The system 100 may be modular, scalable, and configured for rapid installation during construction of a new facility or for a retrofit in a pre-existing facility. The system 100 may be a "multichannel" system, being configured to receive and analyze inputs from multiple air sources and determine the presence of smoke, combustion gasses (e.g., carbon monoxide), elements or compounds indicative of smoke and/or fire, or other harmful elements or compounds in the air received. Accordingly, one multichannel system 100 may be configured to monitor multiple protected areas, while using a single power source, for example. Further, such multichannel systems 100 may be linked together and/or with other monitoring devices via any suitable telecommunications network, e.g., existing network protocols via RS-485, USB or Ethernet connections and/or one or more wireless protocols, and may be linked to an external device, such as a fire panel or a building management system, enabling or otherwise facilitating centralized monitoring. Further, the systems 100 may be configured to provide instructions to the building management systems, so as to promote a rapid response to any emergency situation.

In an embodiment, the system 100 generally includes a rail 102 and one or more backplanes (four are shown in FIG. 1: 104, 106, 108, 110; five are shown in FIG. 2: 104-110 and 112). The backplanes 104-112 and the rail 102 may be coupled, for example, hung, fastened, mounted, or otherwise attached to a wall, so as to be suspended therefrom. In an embodiment, the backplanes 104-112 may be directly fastened to the wall using screws. The rail 102 may serve to facilitate installation and/or accurate alignment of the backplanes 104-112 in a rack, such as a metallic rack. Further, in at least one embodiment, clips may be employed to initially secure the backplanes 104-112 to the rail 102, stabilizing the backplanes 104-112 while the backplanes 104-112 are fastened to the wall. In some embodiments, the rail 102 may be unnecessary and omitted.

Although four backplanes 104-110 are illustrated in FIG. 1, it will be appreciated that fewer backplanes may be used, or additional backplanes (e.g., backplane 112 illustrated in FIG. 2 and/or others) may be employed, for example, to provide for fewer or add additional channels to the system 100, respectively, as will be described below. Further, in embodiments including the rail 102, the rail 102 may be sized to accommodate any suitable number of backplanes 104-112.

In at least one embodiment, each of the backplanes 104-112 may include first and second lateral sides 113, 114 and an outward face 116 extending laterally between the first and second lateral sides 113, 114 and facing away from the rail 102, for example. Further, each of the backplanes 104-112 may include an interconnection port 118 formed on the first lateral side 113, for example, recessed or otherwise offset from the outward face 116. The backplanes 104-112 may also each include an interconnection terminal 120 protruding from the second lateral side 114. The interconnection port 118 and the interconnection terminal 120 may be complementarily shaped, such that the interconnection terminal 120 of each of the backplanes 104-112 is configured to be mated with the interconnection port 118 of an adjacent one of the backplanes 104-112.

It will be appreciated, however, that this is but one embodiment among many contemplated for the interconnection port 118 and interconnection terminal 120. For example, in other embodiments, the interconnection terminal 120 may be provided by a flat cable or plug which is received into one or more recessed connections or sockets, provided by the interconnection port 118.

In an embodiment, the interconnection port 118 and the interconnection terminal 120 may be disposed on the bottom half of each backplane 104-112, and the backplanes 104-112 may be configured to couple with the rail 102 in the top half thereof. In this configuration, the mating of the interconnection port 118 and the interconnection terminal 120 may proceed by a natural hanging motion of each of the backplanes 104-112, fitting together smoothly, or with a snap, click, smoothly, or otherwise, as each adjacent backplane 104-112 is coupled with the rail 102 or otherwise coupled to the wall. Further, the backplanes 104-112 may be configured to couple together prior to being coupled with the wall and/or with the rail 102.

Each interconnection port 118 and each interconnection terminal 120 may be or include one or more electrical contacts. The electrical contacts may be provided for transferring power and/or one or more signals between the backplanes 104-112, enabling communication and/or power transfer between the backplanes 104-112 and, more particularly, the modules associated therewith, as will be described in greater detail below. Further, in some embodiments, the backplanes 104-112 may provide communication between the modules associated therewith and between the modules and external devices. Such communication signals may follow various network protocols, whether the same or different between the two communication links.

Each of the backplanes 104-112 may also include a module port 122, for example, on the outward face 116. The module port 122 may be disposed on the bottom half of the backplane 104-112; however, such positioning is merely one example among many contemplated herein. Further, the module port 122 may include one or more electrical contacts configured to transfer power between and/or communicate with one or more modules coupled with the backplanes 104-112, as will be described in greater detail below. The electrical contacts of the module port 122 may be electrically coupled with the interconnection port 118 and/or the interconnection terminal 120, via the outward face 116 of the backplane 104-112, so as to provide electrical transmission therebetween. Further, the illustrated module port 122 may be representative of any arrangement of one or more electrical contacts, connections, and/or interfaces provided by the backplanes 104-112 for communication with and/or powering associated modules, as will be described below.

Each of the backplanes 104-112 may also include one or more module hangers 124. The module hanger 124 may be a bracket, clip or set of clips, an aperture exposing a portion of the rail 102, a secondary rail, a recess or ledge, or a protrusion extending generally normal to the outward face 116. A variety of configurations for the module hanger 124 are contemplated for use herein. Further, each of the backplanes 104-112 may provide multiple module hangers 124 to facilitate secure and precise alignment of associated modules, as will be described in greater detail below.

Each of the backplanes 104-112 may also include an outlet port 126 and an inlet port 128. The inlet port 128 and the outlet port 126 may be formed in a top side wall 131 of the backplanes 104-112, which may extend generally normal to the outward face 116 thereof. The outlet and inlet ports 126, 128 may each be coupled to a conduit 130, 132, with the outlet port 126 coupling with the conduit 130 and the inlet port 128 coupling with the conduit 132, as shown. The conduits 130, 132 may be air conduits of any type and may couple with the outlet and inlet ports 126, 128, for example, by sliding into the ports 126, 128 using slip couplings, press-fitting, fasteners, gaskets, seals, adapters, and/or the like. The conduit 132, coupled to the inlet port 128, may extend from and one or more protected areas and may receive air therefrom and transmit the air to the inlet port 128. The conduit 130, coupled to the outlet port 126, may receive air from the outlet port 126, and transmit the air to any suitable location, for example, back to the one or more protected areas, to the exterior environment, or to any other area.

The backplanes 104 and 112 positioned at the ends of the provided series of backplanes 104-112 may have an open interconnection port 118 and/or an open interconnection terminal 120. For example, as shown, the backplane 104 may have an open interconnection terminal 120, while the backplane 112 may have an open interconnection port 118. As such, additional backplanes may be provided by coupling the additional backplanes using the empty interconnection port 118 and/or the empty interconnection terminal 120, thereby facilitating expansion of the system 100.

Figure 3:
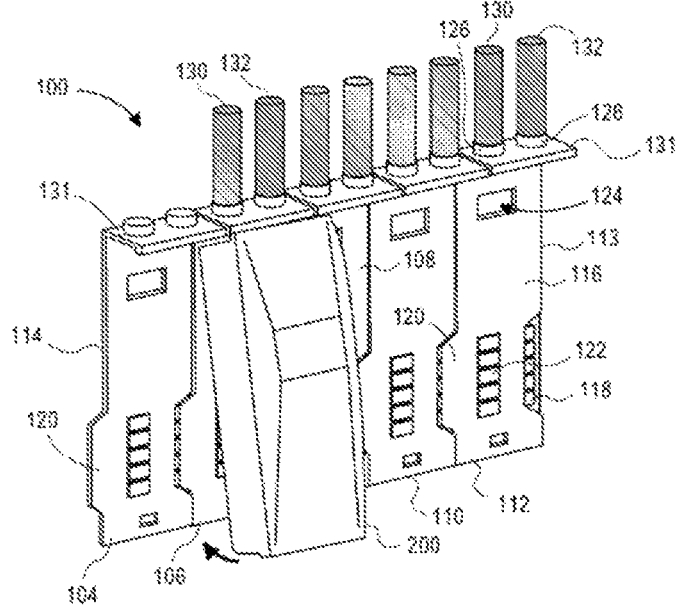
FIG. 3 illustrates another perspective view of the partially-assembled smoke detection system, depicting a detector module being coupled to one of the backplanes, according to an embodiment.
Figure 4:
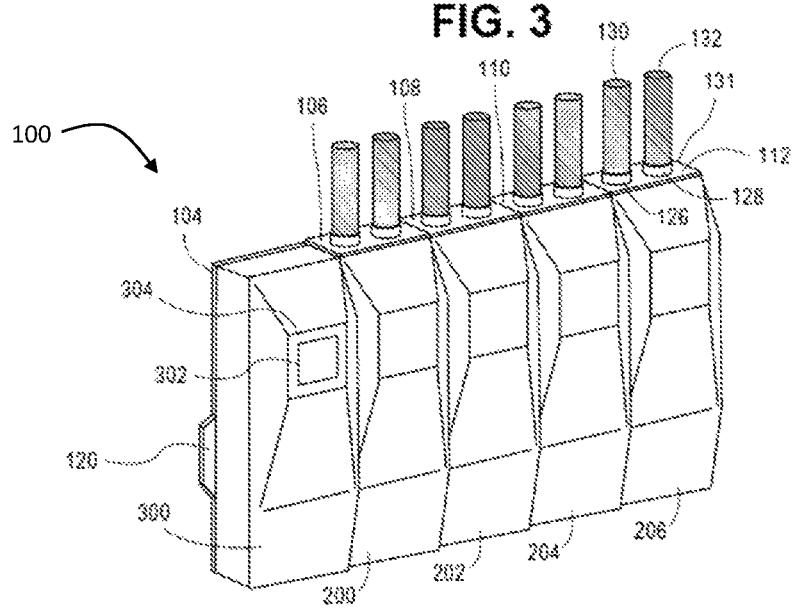
FIG. 4 illustrates a perspective view of the smoke detection system, once assembled, according to an embodiment.

FIGS. 3 and 4 illustrate perspective views of the system 100 at different stages of assembly, according to an embodiment. In particular, FIG. 3 illustrates a detector module 200 being coupled with the backplane 106, and FIG. 4 illustrates the system 100 after coupling the detector module 200, a plurality of additional detector modules 202-206, as well as a display module 300, to the backplanes 104-112, according to an embodiment.

Each of the detector modules 200-206 may be coupled with one of the inlet air conduits 132 via one of the inlet ports 128 and with one of the outlet air conduits 130 via one of the outlet ports 126. Further, the detector modules 200-206 may each include an aspirating fan or blower, housed internally therein, which may be configured to draw air into the detector module 200-206 and exhaust air out of the detector module 200-206 via the air conduits 132, 130, respectively. The detector modules 200-206 may each also include a dust filter to remove particulate matter from the air drawn into the detector module 200-206 and an air flow sensor to monitor the flow rate of the air. Additionally, the detector modules 200-206 may each include a sensing device, such as a laser head or another type of high-sensitivity smoke detection device, configured to sense elements, compounds indicative of smoke in the air, and/or combustion gasses such as carbon monoxide, and provide signals indicative of the same. The sensing device may include a filter to remove particulate matter over a certain size. The detector modules 201-206 may each include a controller and memory to receive, interpret, and/or record such signals.

Each of the detector modules 200-206 may provide one or more interfaces, for example, a user interface, an external interface, and an internal interface, each of which may be configured to provide access to the controller. In at least one specific embodiment, the detector modules 200-206 may include a plurality of LEDs, configured to indicate power, alarm, fault, and disable. Further, the detector modules 200-206 may include two inputs providing supervised voltage detectors and three outputs providing free voltages relays for communications with an external device, such as a fire panel. The inputs of the detector modules 200-206 providing supervised voltage detectors may enable the inputs to recognize a status of another device coupled to the detector module 200-206 therewith. The other device may be, for example, a fire panel. Thus, the input including a supervised voltage detector may be configured to recognize that: a signal is present (input activated), no signal is present (input not activated), an open circuit is exists (broken line between the fire panel and the input), and a short circuit exists (short-circuited line between the fire panel and the detector).

The detector modules 200-206 may also provide a network protocol for communicating the display module 300 and/or external devices (e.g., a fire panel), and may include an external power supply port, for example, configured to receive 24V power from the external power source. These interfaces may all be configured to be integrated with the backplanes 104-112. Further, the backplane 104-112 may also provide connectivity between the display module 300 and an analogue loop for connecting any existing fire panel network protocol.

Since the detector modules 200-206 provide a network protocol, some embodiments of the system 100 may omit the display module 300. In such embodiments, the detector modules 200-206 may operate in a "standalone" mode, providing a direct communication between the detector modules 200-206 and an external device. As such, the detector modules 200-206 may be configured to individually or collectively report signals to a remote fire panel or to other external devices or systems.

When included, the display module 300 may include a user interface, an external interface, an internal interface, a controller, and one or more memory devices associated therewith. The user interface may provide for local interaction between an operator, installer, or the like, with the display module 300. The external interface may provide for integration of the display module 300, and thus the system 100, into a larger system or network, as will be described in greater detail below. The controller and memory devices may process, store, and/or transmit information via any of the interfaces and/or may be employed to control, calibrate, or otherwise configure other components of the system 100. In an embodiment, the display module 300 may not require connection with an air conduit and thus the inlet and outlet ports 128, 126 of the backplane 104 coupled with the display module 300 may not be connected with any air conduits.

Further, the display module 300 may include a display window 302 on an outward face 304 thereof and one or more contacts on an inward face. The contacts on the inward face may be configured to engage or otherwise electrically connect with the module port 122 of one of the backplanes 104-112. In other embodiments, the display module 300 may provide a "minimum display," such that the display window 302 may be substituted with a simple LED or LED array to quickly convey, for example, alarm status, the operation status of the detector modules 200-206, log events, and/or display operational status of the interfaces. The display module 300 in the minimum display may lack a keypad to enable local configuration thereof; thus, the display module 300 may include a port, e.g., a USB port, for coupling with a computer, enabling such configuration.

The display module 300 may also include a mounting member, configured to couple with the module hanger 124 of one of the backplanes 104-112, and/or the rail 102, so as to secure, hang, mount, or otherwise physically couple the display module 300 and the backplane 104. It will be appreciated that the module hanger 124 and the mounting member may be a hook and ledge pairing, one or more magnets, a collet, interlocking members, a dovetail connection, or any other suitable connection or coupling, any of which is contemplated by use of the term "physically couple," as used herein.

The detector modules 200-206 and/or the display module 300 may be configured to communicate with external HSSD systems (whether other systems 100 or conventional HSSD devices) via an external interface integrated with the backplanes 104-112, which may be referred to as SenseNET™. Such external interface may provide for integration of the detector modules 200-206 into a larger system or network, enabling the controller to communicate with external hardware and/or users, for example, obviating a necessity for an intermediary such as the display module 300. The internal interface may provide for communication between the controllers of the detector modules 200-206 and the display module 300.

The system 100 may further define a protocol for communication between the display module 300 and the detector modules 200-206, which may be integrated in the backplanes 104-112. This protocol may be referred to as SenseNET+™, and may be based on a token ring topology without a master. Further, each detector module 200-206 and/or each display module 300 may include at least two inputs: a programmable input disposed proximal the top and a second programmable input for PSU monitoring. In some cases, power supply unit (PSU) monitoring may not be required and, as such, the second programmable input could be programmed for other purposes. The detector modules 200-206 and/or display modules 300 may also include outputs. Each output may be activated by a volt free relay contact placed in the backplanes 104-112, e.g., for optimizing the number of pins in the MCU connector. In an embodiment, the switching contact will use the power supply present in the interconnect board, that is from 18 VDC to 30 VDC.

The backplanes 104-112 may be modular and interchangeable; thus, it will be appreciated that the detector modules 200-206 and the display module 300 may be disposed in any suitable order and to any of the backplanes 104-112, such that any of the backplanes 104-112 are disposed adjacent the first or second lateral side 113, 114 of any of the other backplanes 104-114. Moreover, in an embodiment, the number of backplanes 104-112 may exceed the number of detector modules 200-206 by at least one, to provide the backplane 104 for the display module 300. The backplane 104-112 for receiving the display module 300 may be chosen, for example, according to the location of the conduits 130, 132, such that the backplane 104-112 for the display module 300 may not be aligned with the conduits 130, 132.

Since coupling with the conduits 130, 132 may not be required for the backplane 104 that couples with the display module 300, in some embodiments, the top side wall 131 of the backplane 104 may be removed or omitted, as shown. However, in other embodiments, the top side wall 131 may be retained and not employed or employed for any other reason, such as to increase retention of the display module 200. Further, the system 100 may be configured to operate with one or more of the detector modules 200-206 removed, leaving one or more of the backplanes 104-112 empty but still coupled to the rail 102 and to one or more adjacent backplane(s) 104-112.

Figure 5:
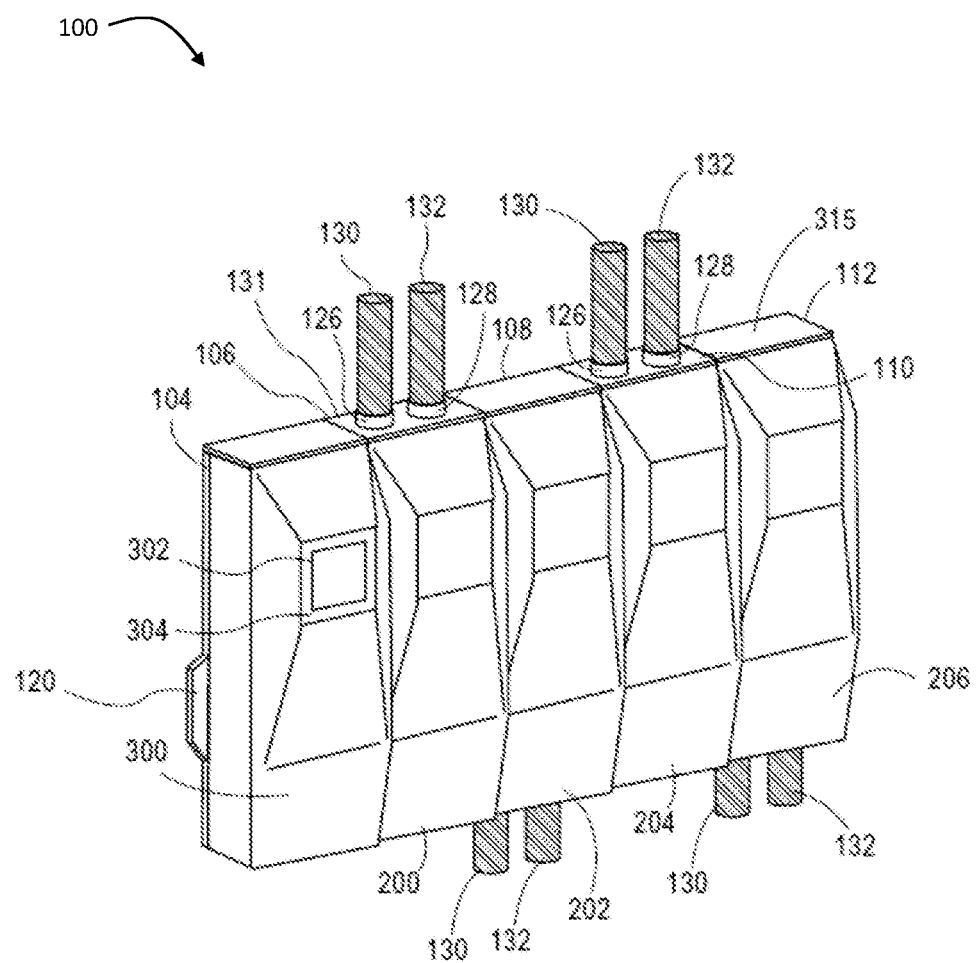
FIG. 5 illustrates a perspective view of a second configuration of the smoke detection system, once assembled, according to an embodiment.

FIG. 5 illustrates a perspective view of a second configuration, among many contemplated, of the system 100 depicted in FIG. 4, according to an embodiment. In FIG. 4, each of the detector modules 200-206 is oriented in a first orientation and configured for connection with the inlet conduit 132 and the outlet conduit 130 on the top side of the system 100. As shown in FIG. 5, however, one or more of the detector modules 200-206 (e.g., detector modules 202 and 206) may be disposed or otherwise oriented in a second orientation. The second orientation may be rotated 180 degrees about a line normal to the outward face 116 (FIGS. 1-3) with respect to the first orientation. Accordingly, one, some, or all of the detector modules (e.g., detector modules 202 and 206) may be configured to connect with the air conduits 130, 132 on the bottom side of the system 100, which may facilitate connection with conduits stemming from multiple different locations and coupling with the system 100.

It will be appreciated that, in the illustrated embodiment, the backplanes 104-112 may not be rotated, but may be capable of connecting with the detector modules 200-206 in either orientation. For example, each of the backplanes 104-112 may provide the top side wall 131 and may also include a bottom side wall (not visible). The top side wall 131 of the backplane modules 108 and 112 connected to the detector modules 202 and 206 in the second orientation may have a blank top side wall 315, which may not be connected to any air conduits. The bottom side walls of the backplanes 106 and 110 connected to the detector modules 200 and 204 in the first orientation may similarly be blank. The inlet and outlet ports 128, 126 may be punched or otherwise formed through the top or bottom side walls, as desired to facilitate easy alignment with the conduits 130, 132. As such, each backplane 104-112 provides connections to conduits 130, 132 on both the top and bottom sides, without requiring rotation of the backplane 104-112. In other embodiments, the top side wall 131 may be removable and configured to couple (e.g., fasten) to either the top or bottom of the backplanes 104-112.

For example, one, some, or each of the detector modules 200-206 may have two different sets of contacts for electrically connecting with the module port 122 (FIGS. 1-3) of the backplane 104-112. In other embodiments, the module port 122 of the backplanes 104-112 may be generally symmetric about a horizontal centerline of the backplane 104-112, enabling a single set of contacts to be used in such reversible detector modules 200-206 in either the first or second orientations. Additionally, the detector modules 200-206 may include a mounting member configured to engage the module hanger 124 (FIGS. 1 and 2).

It will be appreciated that features of any of the described embodiments of the detector modules 200-206 and/or backplanes 104-112 may be combined into a single embodiment thereof. Further, although two orientations are depicted for the detector modules 200-206, it will be appreciated that a range of orientations is contemplated. Further, the system 100 may be mounted to a vertical or inclined wall, a ceiling or a floor. The two orientations, however, are generally taken with reference to the backplanes 104-112 and thus, may apply irrespective of the orientation of the surface to which the backplanes 104-112 are attached.

Referring now generally to FIGS. 1-5, in exemplary operation, each of the detector modules 200-206 may receive and monitor air, and thus each may provide a separate "channel" in the system 100. For example, each detector module 200-206 of the system 100 may be configured to receive and monitor air from separate protected areas. However, in some instances, multiple detector modules 200-206 or "channels" may be allocated to a single protected area, for example, to provide redundancy in case one of the detector modules 200-206 fails. Further each detector module 200-206 may provide a closed portion of an air flowpath, such that leakage or "crosstalk" between the flowpaths of the detector modules 200-206 is avoided and/or eliminated.

The number of channels desired may be pre-selected. Once the desired number of channels is determined, a number of backplanes 104-112 may be selected, which may generally be at least one more than the number of channels. A number of detector modules 200-206 may also be selected, which may correspond to the number of channels desired. It will be appreciated that the number of detector modules 200-206 "corresponding" to the number of channels does not necessarily require a 1:1 relationship, as two or more detector modules 200-206 may be provided for a single channel and/or two or more channels may be monitored by a single detector module 200-206. Moreover, in embodiments in which different types of detector modules 200-206 are employed for the first and second orientations, the number of each type of detector modules 200-206 may also be determined.

The backplanes 104-112 may then be secured to the wall, for example, using the rail 102 to facilitate such installation, as depicted in FIG. 1. The display module 300 may then be attached to one of the backplanes 104-112, e.g., the backplane 104, as shown. Before, during, or after attaching the display module 300, the selected number of detector modules 200-206 may be attached, in the desired orientation, and connected with the air inlet and outlet conduits 130, 132, via the inlet and outlet ports 128, 126 of the backplanes 104-112.

Once the display module 300 and detector modules 200-206 are in place, power may be supplied to the system 100. Power and signals may be transferred between the backplanes 104-112 via the mated interconnection ports 118 and interconnection terminals 120. Further, power and/or signals may be routed from the backplanes 104-112 to the display module 300 and/or the detector modules 200-206 via the module port 122.

The display module 300 may receive instructions from a user, an external system, or the like, which may be used to configure the detector modules 200-206, passing such signals between the display module 300 and the detector modules 200-206 via the backplanes 104-112. When on-line, the detector modules 200-206 may monitor air from the protected areas, record events, and/or provide signals indicative of such monitoring (e.g., upsets, alarms, etc.) to the display monitor 200 and/or to an external device, such as a fire panel. The display module 300 may be coupled with a detector management device, such as a building management system, a graphical user interface, an external computer or controller, a master controller, a screen, another device, and/or a combination thereof and may relay the monitoring information to this detector management system.

It will be appreciated that the modular design of the system 100 may enable the system 100 to be scalable, with the number of channels being selectable, and the system 100 being readily assembled from modular components to accommodate any number of channels selected. The provision of multiple channels, in and of itself, may be beneficial to condense the location of monitoring equipment and reduce the number of power sources. Further, the modular design may provide additional flexibility, for example, if additional channels are contemplated but not yet required, one of the backplanes 104-112 may be left empty, while the system 100 is still configured to operate normally with the detector modules 200-206 currently included. Later, an additional detector module may be added, when needed. Further, the system 100 may also be contracted by removing one of the detector modules 200-206, e.g., one of the detector modules (as shown, 206) on the end of the system 100. The associated backplane 112 may also be removed, or may be left in place. As such, the system 100 may be configured to add or subtract one or more detector modules 200-206, and one or more backplanes 104-112, without reconfiguring of the remaining backplanes 104-112, the remaining detector modules 200-206, the display module 300, or a combination thereof.

As the term is used herein, "reconfiguring" is generally defined to mean adjustment to the hardware (e.g., circuitry). Accordingly, when a backplane 104-112 or detector module 200-206 is added (expanding the system 100) or removed (contracting the system 100) "without reconfiguring" other components, such adjustment is made generally without necessitating any other substantial structural changes to the system 100. However, additions such as caps, fasteners, etc. consistent with the system 100 having a new "end" according to such contraction or expansion, may be provided without departing from the scope of "without reconfiguring."

Moreover, the backplanes 104-112 may each have substantially the same construction, such that the backplanes 104-112 may be characterized as being "interchangeable," In other words, in an embodiment, the five illustrated backplanes 104-112 may proceed in any order, as each may be configured to fit with each other. Further, the module hanger 124 and module port 122 of each of the backplanes 104-112 may be configured to couple with the display module 300 or any one of the detector modules 200-206.

Moreover, the modularity of the system 100 may facilitate installation by providing flexibility for placement of the air conduits 130, 132. Since multiple channels may be provided, enabling centralized monitoring of several areas, the conduits 130, 132 may originate in different directions from the system 100. As noted, above, the detector modules 200-206 may be configured to take one of at least two orientations, without necessarily requiring rotation of the backplanes 104-112, which may avoid having to route the air conduits (and/or electrical conduits) around the system 100 and to the top thereof. Additionally, such modularity may facilitate installation of electrical components, including, for example, power supply prior to powering on the detector modules 200-206 and/or the display module 300. This may allow for current and/or voltage checking of the system 100, prior to connecting sensitive electrical components to the power source.

Figure 6:
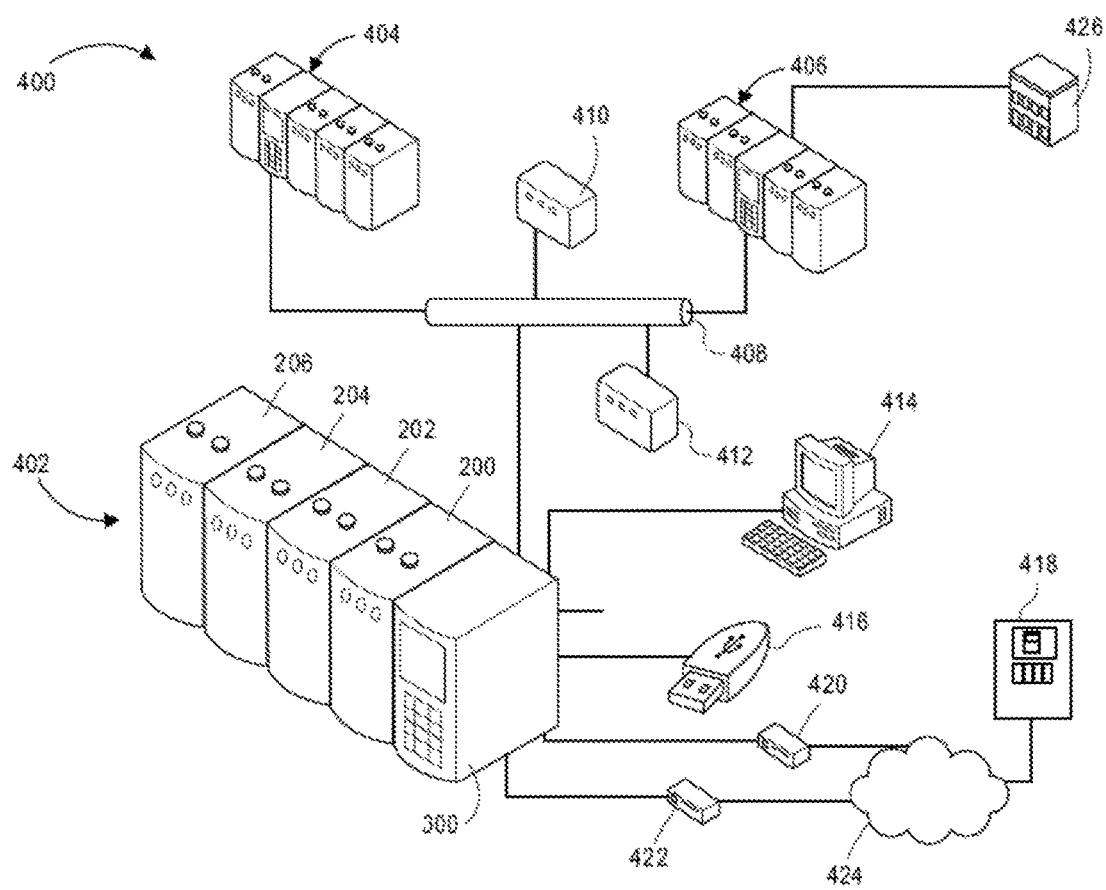
FIG. 6 illustrates a schematic view of a smoke detection network, according to an embodiment.
Figure 7:
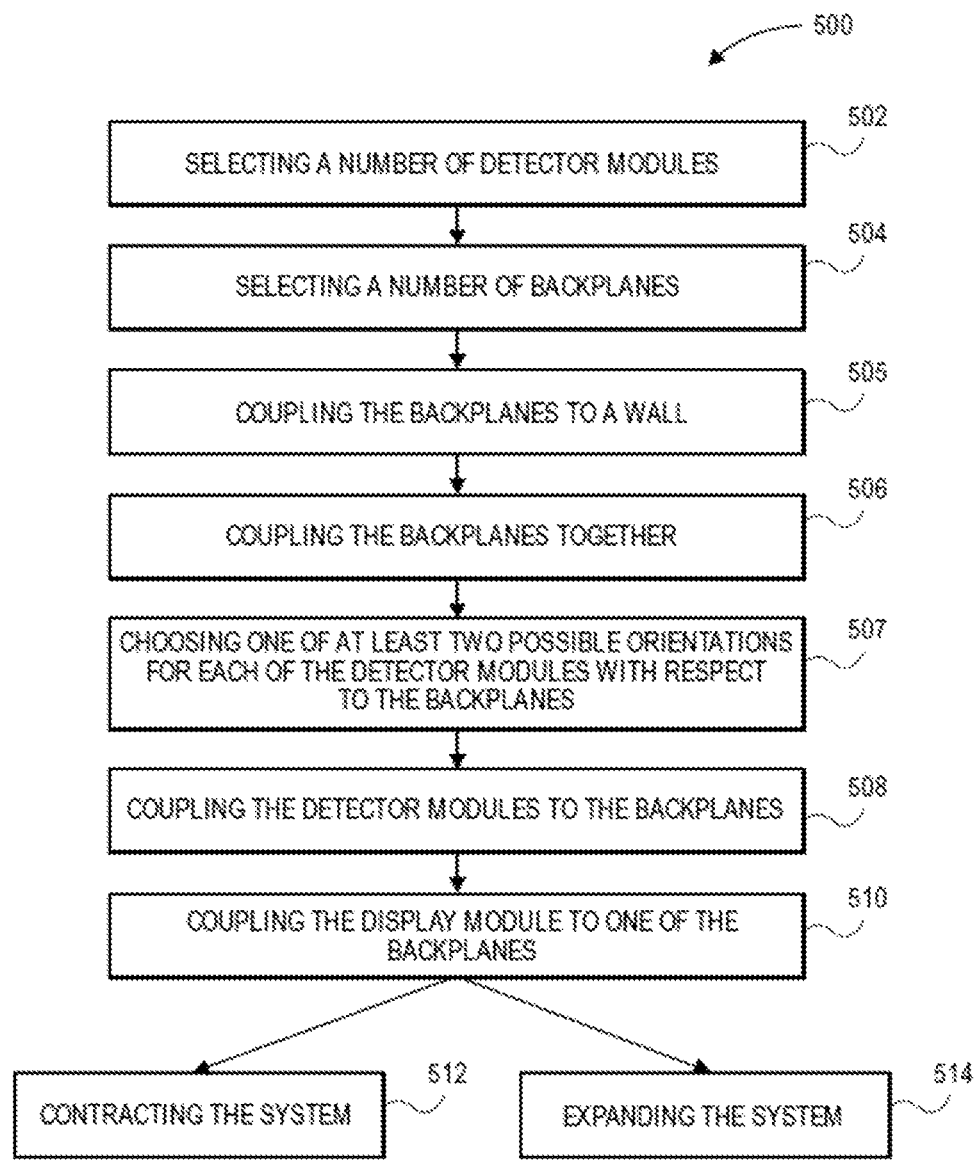
FIG. 7 illustrates a flowchart of a method for assembling a smoke detector, according to an embodiment.

FIG. 6 illustrates a schematic view of a smoke detection network 400, according to an embodiment. The network 400 may include three or more module "clusters" (three are shown: 402, 404, 406). Each cluster 402, 404, 406 may be provided by one or more embodiments of the system 100 shown in and described above with reference to FIGS. 1-5, and thus may include the display module 300 and one or more of the detector modules 200-206, as indicated for cluster 402. Each of the clusters 402, 404, 406 may be configured to receive and monitor air from separate protected areas, and may each include any number of detector modules 200-206.

The clusters 402, 404, 406 may be linked together via a network 408, which may include one or more computers, servers, junctions, or the like, and may be, for example, an Ethernet or one or more wireless links. The network 408 may be a closed network or may include, for example, a secured connection via the internet. One or more, for example, as shown, two conventional smoke detectors 410, 412 may also be linked to the network 408. The conventional smoke detectors 410, 412 may or may not be classified as "high-sensitivity" smoke detectors, as the term is known in the art, and may be configured to receive and monitor air from secondary protected areas, for example, if the clusters 402, 404, 406 are introduced to the system 400 as a retrofit. In other embodiments, the conventional smoke detectors 410, 412 may be used as a back-up or redundant monitoring, in addition to the clusters 402, 404, 406.

The display module 300 of one, some, or all of the clusters 402, 404, 406 may include one or more ports for input and/or output with external devices. For example, the display module 300 of the cluster 402 may include a universal serial bus (USE) or Ethernet connection with a controller (e.g., computer) host 414, which may be accessible to a user, for example, an installer. The user may be able to access the cluster 402, for example, the controller of the display module 300, using the controller host 414. The display module 300 may also include, e.g., a USE connection with a computer-readable storage medium, such as flash or memory drive 416, which may record a monitoring history of the cluster 402 and/or provide executable instructions to the display module 300, facilitating implementation of upgrades to the display module 300 and/or the detector modules 200-206. The display module 300 may also be coupled with a fire panel 418, for example, via an analogue protocol interlace card (APIC) such as an encoder 420 or decoders 422, and one or more analog loops 424. It will be appreciated that the display module 300 may only communicate with one APIC at a time, and thus the depicted connection with the encoder 420 and decoder 422 may represent the ability to connect to either the encoder 420 or the decoder 422. Further, there may be six or seven different loop protocols corresponding to the different of fire panels and provided as part of the analogue loop 424.

The clusters 402, 404, 406 may be controlled in a token ring network topology. In other embodiments, the clusters 402, 404, 406 may be controlled in any other network topology, e.g., in one or more "master-slave" relationships. Although such master-slave topology may be slower than a token ring network topology, such a master-slave topology may allow for backwards compatibility with the conventional smoke detectors 410, 412. For example, the slave clusters 402, 404 and/or the convention smoke detectors 410, 412 may report to the master cluster 406. The master cluster 406 may, in turn, report to an overall building management system 426, for example, via a building management system protocol (BMS), or in some other cases, via a USE or Ethernet connection. Further, the display modules 300 may be able to control and/or monitor a variety of systems, including the building management system, for example, mechanical and/or electrical equipment such as ventilation systems, lighting and/or power systems, security systems, tire systems, e.g., as part of the building management system, and the like. Various protocols, such as TAP, ASCII, BACnet, and MODbus, at least, may also be supported. The master cluster 406 may monitor the building management system 426 and/or provide instructions thereto.

With additional reference to FIGS. 1-5, FIG. 7 illustrates a flowchart of an exemplary method 500 for installing a smoke detector, such as the modular system 100. The method 500 may include selecting a number of detector modules 200-206, as at 502. In an embodiment, the number of detector modules 200-206 may correspond to a number of channels selected for the system 100. The detector modules 200-206 may be configured to receive air from a protected area and detect smoke and/or compounds indicating smoke and/or fire in a protected area.

The method 500 may also include selecting a number of backplanes 104-112, as at 504 and coupling the backplanes 104-112 and a rail 102 to a wall, as at 505. In an embodiment, the number of backplanes 104-112 may be at least one more than the number of detector modules 200-206. The method 500 may also include coupling the backplanes 104-112 together, as at 506, such that the backplanes 104-112 are at least electrically coupled together. In an embodiment, the backplanes 104-112 may also be physically coupled together and/or may be remotely coupled together, for example, distributed up to 12 kilometers apart.

The method 500 may also include choosing an orientation from a selection of at least two possible orientations for each of the detector modules 200-206 with respect to the backplanes 104-112, as at 507. It will be appreciated that the backplanes 104-112 themselves may be located on a floor, vertical or inclined wall, or ceiling in any orientation desired. For example, the method 500 may include orienting a first one of the detector modules 200-206 (e.g., display modules 200 and 204 in FIG. 5) in a first orientation, and orienting a second one of the detector modules 200-206 (e.g., detector modules 202 and 206 in FIG. 5) in a second orientation, wherein the first and second orientations are 180 degrees apart. In at least some embodiments, the display module 300 may not be rotatable.

Further, the method 500 may include coupling the detector modules 200-206 to the backplanes 104-112, as at 508. Each of the detector modules 200-206 may be coupled to a separate one of the backplanes 104-112. Further, the method 500 may include coupling the display module 300 to one of the backplanes 104-112, as at 510. The display module 300 may be communicable with one or more of the detector modules 200-206 via two or more of the backplanes 104-112.

In an embodiment, the method 500 may also include contracting the system 100, as at 512. For example, contracting at 512 may include removing one of the detector modules 200-206 from one of the backplanes, as at 512. Although one of the backplanes 104-112 may thus be missing, the system 100 may still be operable. Further, the method 500 may include expanding the system 100, as at 514. Expanding at 514 may include coupling an additional backplane to the backplanes 104-112, and coupling an additional detector module 200-206 to the additional backplane 104-112, such that the display module 300 is communicable with the additional detector module 200-206.

In an embodiment, the number of detector modules 200-206 may be limited, for example, by the number of paths provided in each of the backplanes 104-112 and/or by the capabilities of the display module 300. In at least one specific embodiment, the number of detector modules 200-206 may be less than or equal to eight. In some embodiments, one or more of the detectors 200-206 may be "distributed"; that is, located remotely from the other detectors 200-206. Additionally, the method 500 may also include coupling the display module 300 with one or more detection management devices, for example, the building management system 426, the controller host 414, and/or the master cluster 406. It will be appreciated that such detection management devices may be coupled to one or more other display modules, for example, display modules of other clusters 402-406. Such connection may be made by any desired telecommunication and/or networking devices or equipment.

While the present teachings have been illustrated with respect to one or more implementations, alterations and/or modifications may be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings.

It will be appreciated that structural components and/or processing stages may be added or existing structural components and/or processing stages may be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein.

The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side," "higher," "lower," "over," "top," and "under" are defined with respect to the conventional plane or working surface being on the top surface of the workpiece, regardless of the orientation of the workpiece.

What is claimed is:

1. An apparatus for detecting smoke in an area, comprising:
   a first detector module comprising a sensor configured to detect smoke in a first volume of air received from the area;
   a second detector module comprising a sensor configured to detect smoke in a second volume of air received from the area;
   a first backplane electrically coupled to the first detector module; and
   a second backplane electrically coupled to the second detector module and to the first backplane so as to transmit power, signals, or both between the first and second detector modules, wherein the first and second backplanes are interchangeable and the first and second detector modules are interchangeable.

2. The apparatus of claim 1, wherein the first and second backplanes each include a first lateral side and a second lateral side, the first backplane being positionable adjacent either lateral side of the second backplane.

3. The apparatus of claim 2, wherein the first detector module is physically coupled with the first backplane, the second detector module is physically coupled with the second backplane, and the first and second backplanes are physically coupled together.

4. The apparatus of claim 2, wherein the first and second backplanes each comprise an interconnection port positioned on the first lateral side, and an interconnection terminal positioned on the second lateral side, wherein the interconnection port of the first backplane is configured to mate with the interconnection terminal of the second backplane when the first backplane is positioned adjacent the first lateral side of the second backplane, and the interconnection terminal of the first backplane is configured to mate with the interconnection port of the second backplane when the first backplane is positioned adjacent the second lateral side of the second backplane.

5. The apparatus of claim 2, further comprising a third backplane electrically coupled with at least one of the first and second backplanes and comprising first and second lateral sides, an interconnection port on the first lateral side, and an interconnection terminal on the second lateral side, wherein the third backplane is interchangeable with the first and second backplanes.

6. The apparatus of claim 5, wherein one of the second and third backplanes is removable from electrical communication with the first backplane, while the other one of the second and third backplanes remains in electrical communication with the first backplane.

7. The apparatus of claim 5, further comprising a display module including a display window, the display module being electrically and physically coupled to the third backplane and configured to receive data from the first and second detector modules, the display module configured to display information indicative of the data received from the first and second detector modules.

8. The apparatus of claim 7, wherein the display module is coupled with a building management system and is configured to provide instructions thereto.

9. The apparatus of claim 7, wherein one of the first and second detector modules is removable while the other one of the first and second detector modules continues to operate.

10. The apparatus of claim 7, wherein the first and second detector modules are configured to be disposed in the same orientation or 180 degrees apart, without disconnecting the second and third backplanes.

11. The apparatus of claim 7, wherein the first and second detector modules are configured to prevent crosstalk of air proceeding therethrough.

12. The apparatus of claim 1, further comprising a plurality of detector modules including the first and second detector modules and a plurality of backplanes including the first and second backplanes and an empty backplane, wherein a number of the plurality of detector modules are coupled to some of the plurality of backplanes, and the apparatus is configured to be scalable by coupling an additional one of the plurality of backplanes to the empty backplane.

13. A method for assembling a smoke detection system, comprising:
   selecting a number of detector modules, wherein the number of detector modules corresponds to a selected number of channels for the smoke detector, the detector modules each being configured to receive air from an area and to detect smoke therein;
   selecting a number of backplanes, wherein the number of backplanes is at least one more than the number of detector modules, and wherein the backplanes are interchangeable;
   connecting at least two of the backplanes together such that the backplanes are at least electrically coupled together; and
   coupling the detector modules to the backplanes, wherein each detector module is coupled to a separate one of the backplanes.

14. The method of claim 13, further comprising distributing at least one of the backplanes remotely from at least one other of the backplanes.

15. The method of claim 13, wherein coupling the at least two of the backplanes together comprises physically and electrically coupling the at least two of the backplanes together by mating an interconnection port of at least one of the backplanes with an interconnection terminal of at least another one of the backplanes.

16. The method of claim 13, further comprising:
removing one of the detector modules from one of the backplanes; and
operating the system with the one of the detector modules removed.

17. The method of claim 13, further comprising:
coupling an additional backplane to the backplanes; and
coupling an additional detector module to the additional backplane, such that the display module is communicable with the additional detector module.

18. The method of claim 13, further comprising choosing an orientation for each of the detector modules from at least two orientations, the detector modules being configured to be coupled to the backplanes in any of the at least two orientations.

19. The method of claim 13, further comprising:
expanding the smoke detection system by coupling one or more additional backplanes to at least one of the backplanes, without reconfiguring the backplanes; and
contracting the smoke detection system by removing one or more of the detector modules, without reconfiguring the remaining detector modules.

20. The method of claim 19, wherein contracting further comprises removing one or more of the backplanes without reconfiguring the remaining backplanes.

* * * * *